United States Patent
Lo et al.

(10) Patent No.: US 7,247,169 B1
(45) Date of Patent: Jul. 24, 2007

(54) KIT OF SPINE GAUGE BLOCKS AND A TOOL ASSEMBLY

(75) Inventors: Janzen Lo, Allentown, PA (US); Chad E. Ryshkus, Dover, WI (US); Neffrey C. Wang, Sherman Oaks, CA (US)

(73) Assignee: Aesculap Implant Systems, Inc., Center Valley, PA (US)

( * ) Notice: Subject to any disclaimer, the term of this patent is extended or adjusted under 35 U.S.C. 154(b) by 389 days.

(21) Appl. No.: 10/783,430

(22) Filed: Feb. 23, 2004

(51) Int. Cl.
*A61F 2/44* (2006.01)

(52) U.S. Cl. .............................. 623/17.11; 623/17.16; 606/61

(58) Field of Classification Search .................. 606/61; 623/17.11, 17.16; 604/117
See application file for complete search history.

(56) References Cited

U.S. PATENT DOCUMENTS

| | | | | |
|---|---|---|---|---|
| 4,566,466 A | 1/1986 | Ripple | | 128/781 |
| 4,834,757 A | 5/1989 | Brantigan | | 623/17 |
| 4,877,020 A | 10/1989 | Vich | | 128/92 |
| 4,878,915 A | 11/1989 | Brantigan | | 623/17 |
| 5,015,247 A | 5/1991 | Michelson | | 606/61 |
| 5,514,180 A | 5/1996 | Heggeness | | 623/17 |
| 5,683,464 A | 11/1997 | Wagner | | 623/16 |
| 5,716,415 A | 2/1998 | Steffee | | 623/16 |
| 6,113,639 A | 9/2000 | Ray | | 623/11 |
| 6,132,465 A | 10/2000 | Ray | | 623/17.11 |
| 6,143,033 A | 11/2000 | Paul | | 623/17.11 |
| 6,165,219 A | 12/2000 | Kohrs | | 623/17 |
| 6,277,149 B1 | 8/2001 | Boyle | | 623/17.16 |
| 6,371,988 B1 * | 4/2002 | Pafford et al. | | 623/17.11 |
| 6,447,544 B1 | 9/2002 | Michelson | | 623/17 |
| 6,478,823 B1 | 11/2002 | Michelson | | 623/17.16 |
| 6,491,724 B1 | 12/2002 | Ferree | | 623/17.11 |
| 6,530,955 B2 | 3/2003 | Boyle | | 623/17.11 |
| 6,984,245 B2 * | 1/2006 | McGahan et al. | | 623/17.11 |
| 2002/0013624 A1 * | 1/2002 | Michelson | | 623/17.16 |
| 2003/0139812 A1 * | 7/2003 | Garcia et al. | | 623/17.11 |
| 2004/0133279 A1 * | 7/2004 | Krueger et al. | | 623/17.16 |

* cited by examiner

Primary Examiner—Paul B. Prebilic
(74) Attorney, Agent, or Firm—RatnerPrestia

(57) ABSTRACT

An assembly of a gauge block and tool for determining the size and shape of space between two adjacent vertebrae. There are a plurality of gauge blocks of different sizes and shapes for determining the vertebral space for subsequent insertion of a permanent artificial spinal disc. As such, a kit with vertebral gauge blocks is disclosed. A method of providing the assembly is also included herein.

13 Claims, 2 Drawing Sheets

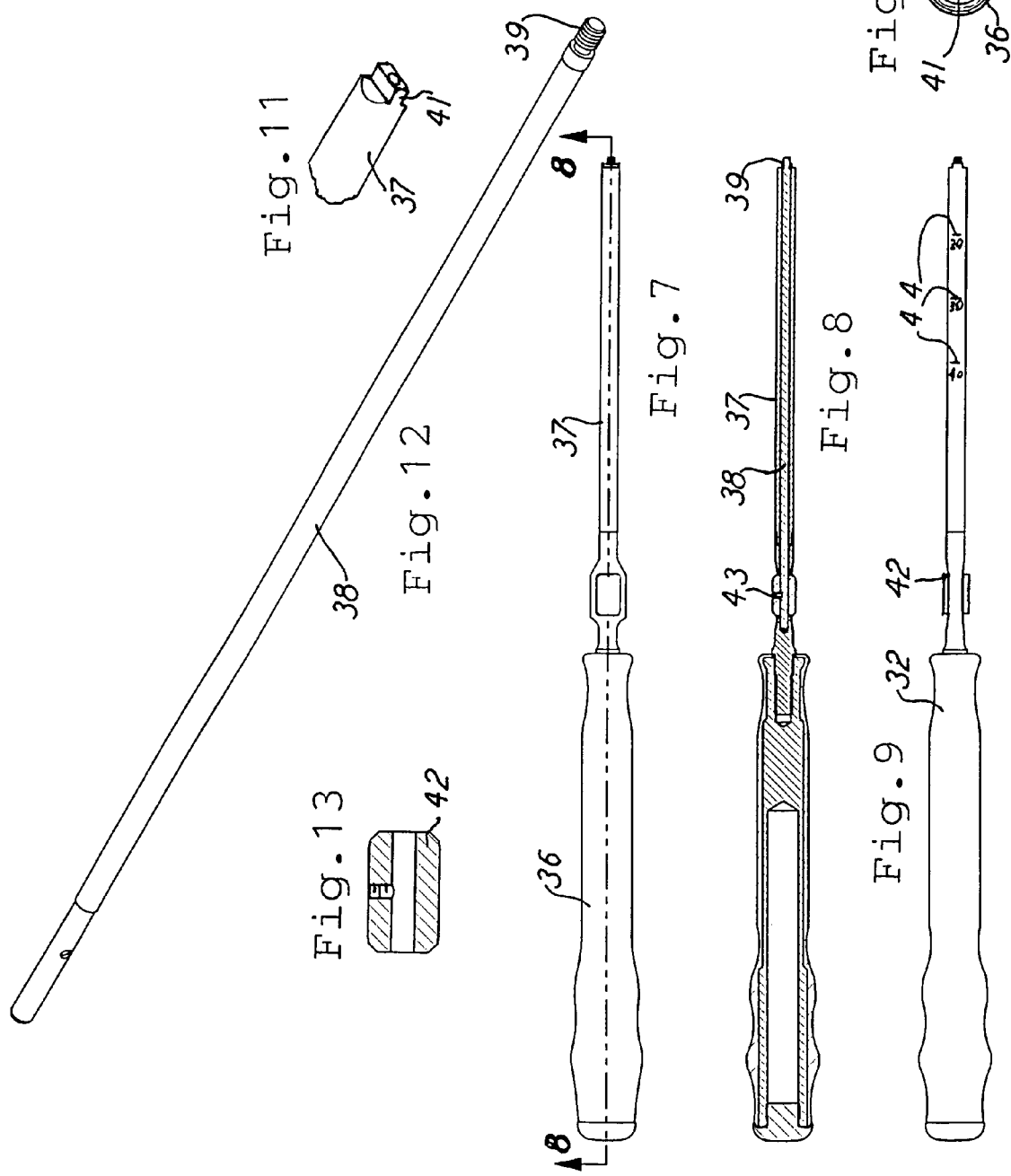

KIT OF SPINE GAUGE BLOCKS AND A TOOL ASSEMBLY

A kit of spine gauge blocks and a tool whereby the distance between two adjacent surfaces in two adjacent vertebrae can be determined. The surgical approach can be accomplished while moving the gauge block into the patient's body without interference from the patient's body parts, such as the patient's aorta, for instance. There can be two different paths of entry into the patient's body, to avoid the body parts. Also included are a method of presenting the assembly of the spinal gauge blocks and the tool and of achieving the mentioned procedure.

BACKGROUND OF THE INVENTION

Human spines are commonly prepared for implanting an artificial disc between two adjacent vertebrae which present two adjacent surfaces facing each other along the spinal column. The procedure of implanting an artificial disc is performed by a surgeon when a person's natural disc is defective. There may be a ruptured or herniated natural disc, and thus the need for the surgical repair consisting of the replacement of the natural disc with an artificial disc. The artificial disc may be man-made and of metal or plastic materials, and its size and shape should be that of the natural disc where the surgery is to restore the spine to a healthy condition.

The space between the two adjacent vertebrae surfaces which face each other along the spinal column is first cleaned by the surgeon and the remaining cleaned space is then to be gauged to determine the height and the angulation between those two surfaces. That is preparatory for the insertion of an artificial disc implant which should snugly occupy the space for desired spinal supportive action.

It is an object of this invention to accurately and efficiently determine the size of that cleaned spaced so that a most appropriate size and shape of artificial implant can be positioned between the two vertebrae. Because this disc implant surgery is approached from the anterior of the patient's torso, it is necessary to negotiate the patient's body parts which normally lie on the path extending from the anterior to the spine. For instance, for the site between the patient's fifth lumbar vertebra and the adjacent first sacral vertebra that site can be approached along a frontal line from the anterior to that site. Therefore, one tool and trial or gauge block arrangement can be employed for accessing that site.

However, other sites along the spine, and the lordotic ones are the ones under consideration herein, that is, those along both the lumbar and cervical spinal lengths, may require an approach which is laterally offset from the full anterior frontal approach mentioned above. That offset is with regard to the approaches, except the one mentioned above, where the patient's aorta is on the access line between the anterior and the spine site.

To accomplish the aforementioned two approaches, this invention provides for two lines between the anterior and the vertebrae sites. This provides for the accurate gauging of the site space height and the tapered angulation between the vertebrae surfaces as they exist on the lordotic vertebrae. A kit of a plurality of different sizes and shapes of gauge blocks or trials, and one tool which can fit all the blocks, can be provided to achieve the implanting of the variety of implant sizes required for optimum restoration of the lordosis of the spine. In the ultimate, there can be a first plurality of blocks which have only one maximum height but which have different angulations or tapers for determining the lordotic angulation of various first sites which are at that one height. Then there can also be a second plurality of blocks at a second height and with their different angulations or tapers for determining the lordotic angulation for various second sites different from the first various sites. Additional pluralities of blocks can also be provided.

The gauge blocks or trials of this invention are provided in kit arrangement in that they are in a plurality and are selected by the surgeon for individual use in determining the size of the vertebrae space in which an artificial implant is to be placed for permanent installation. Thus, the surgeon can select the optimum height and shape or taper of the implant after the surgeon has explored the site by sensing with the gauge block. In those instances, the sites are of the tapered lordotic shape, and therefore they are in the lumbar and cervical lengths of the spine. That shape is such that the space is higher at the anterior side of the spine, compared to the posterior side, that is, it is tapered down to the rear of the spine. According to the patient, the height and taper of any particular site can differ from that of another patient. So, for instance, a collection of say six blocks, all at a maximum height of say 11 mm at the highest location of the taper, can each have their own individual angulation of taper, such as 4, 5, 6, 7, 8, and 9 degrees. Other heights and angulations can also be provided to match the variety of vertebrae spacing and patients.

Further, each block can be arranged for accommodating the two angularly related anterior approaches, thus the kit is doubled in its versatility for the various approaches. Still, each gauge block can be inverted for spinal approaches from either lateral side of the patient.

Both the assembly of the blocks with the tool and the method of producing and applying same are disclosed herein.

BRIEF DESCRIPTION OF THE DRAWINGS

FIG. 7 is a side elevation view of the tool used with the block shown herein.

FIG. 8 is a section view along a plane designated by the line 8—8 on FIG. 7.

FIG. 9 is a top plan view of the tool shown in FIG. 7.

FIG. 10 is an end elevation view of FIG. 9.

FIG. 11 is an enlarged perspective view of the right end of the tool shown in FIG. 9.

FIG. 12 is an enlarged perspective view of an interior part of the tool shown in FIG. 8.

FIG. 13 is an enlarged section view of a part of the tool shown in FIG. 8.

DETAILED DESCRIPTION OF THE PREFERRED EMBODIMENT AND METHOD

Figure 1:
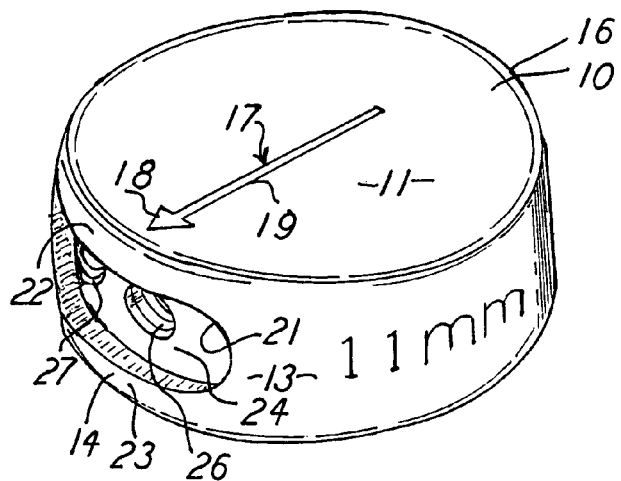
FIG. 1 is a perspective view of a gauge block of this invention.
Figure 2:
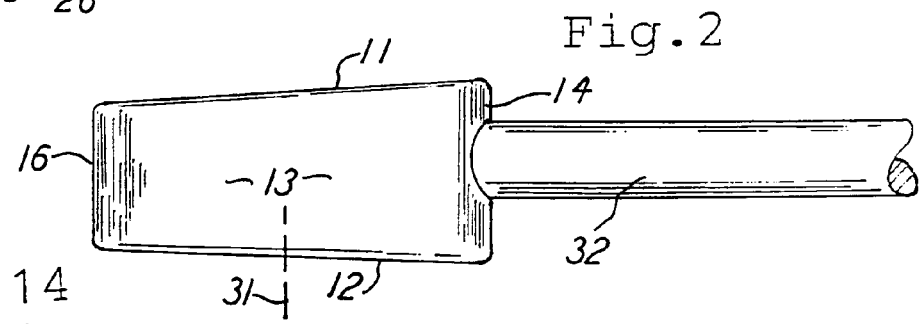
FIG. 2 is a side elevation view of the block of FIG. 1, and showing a fragment of the tool attached.
Figure 6:
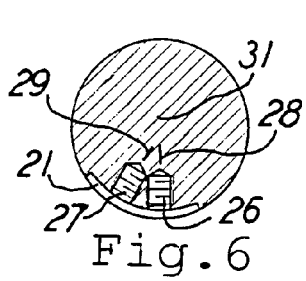
FIG. 6 is a section view along a plane designated by the line 6—6 on FIG. 5.
Figure 3:
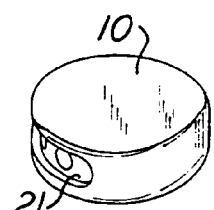
FIG. 3 is a perspective view of the block of FIG. 1, but on a reduced scale.

FIG. 1 shows a gauge block 10 of this invention, and it is seen, as in FIG. 6, as having a cylindrical configuration in a top view thereof. There are two spaced-apart and planar surfaces 11 and 12, such as shown in FIG. 2 where the block 10 is more clearly shown as having a tapered shape. The block 10 also has an encompassing peripheral surface 13 extending completely around the side of the block 10 and between the two surfaces 10 and 11. In the configuration of the block 10 as shown herein, the surface 13 is an endless side of the block and is circular in its shape. The block 10 is preferably a solid piece. The surfaces 11 and 12 are planar and completely smooth by being free of any projections.

Being of a taper or wedge shape, a location on the block at 14 presents a height which is greater than the height at a location designated 16. Those two locations 14 and 16 are therefore respectively at the maximum and minimum heights of the block 10, and they are on diametrical opposite sides of the block 10. An indicia, in the shown form of an arrow 17, is affixed on the block surfaces 11 and 12, such as shown on the surface 11. There is an arrow head 18 which is pointing to the location of the maximum height 14. The arrow has a stem portion 19 which is aligned with the tapered shape of the block 10. The surface 12 of the block 10 can also have indicia, such as indicia 17, aligned with the taper. Of course, other indicia could be applied to indicate the orientation of the taper of the block 10.

FIGS. 1, 3, 5, and 6 also show there is a groove or relief 21 in the surface 13, and it extends in the height direction to be spaced from the two surfaces 11 and 12. That is, there are lips 22 and 23 of the wall or surface 13 intervening between the surfaces 11 and 12, respectively. The relief terminates in a blind wall 24. Thus, there is a counter-sunk portion in the side surface 13 of the block 10, and that is one portion of a tongue-and-groove connection.

Figure 5:
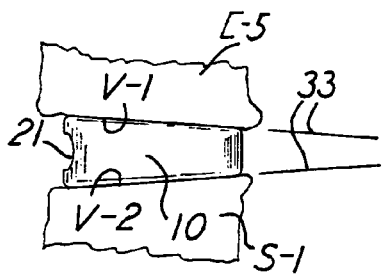
FIG. 5 is a side elevation view of FIG. 3.

The wall 24 has two holes 26 and 27 extending therein, and they are shown as threaded holes with respective central axes 28 and 29 directed to the central longitudinal axis 31 of the block 10, all as best shown in FIGS. 5 and 6. The hole 26 is aligned with the taper indicia 17 to be on the same upright plane therewith. The hole 27 is angulated relative to the indicia 17, and it is thus angulated to the orientation of the taper of the block 10. However, both holes 26 and 27 extend radially, and that is each is axially aligned, with the central axis 31 of the block 10, as shown in FIG. 6.

A tool 32, fully described later, can be releasably connected to the block 10 by threading into either of the two holes 26 or 27, at the election of the surgeon. With the two holes 26 and 27, the surgeon can approach the patient's spine from the patient's anterior. By making the elected threaded connection in the hole 26 there can be a frontal approach, and by using the hole 27 there can be an oblique or angulated approach. In both approaches, the smaller height at 16 will be in the desired leading position in moving toward the spine. The election of the approach to be employed will be determined by the clearance or obstruction presented by parts of the patient's body along a line from the anterior to the spine and according to which vertebra is accessed. Tool 32 extends only within the planes of the surfaces 11 and 12.

FIG. 1 shows the block is marked with the size of 11 mm, and that is the dimension of the maximum height at 14. This invention provides for a plurality of the blocks of the 11 mm height, but each one of that plurality will have a different angulation of the taper. That, is, one can be at a four-degree taper, another at a five-degree taper, and so on through series of 11 mm blocks. Then there can be another series of blocks with a different height of say 13 mm, and each of that series can have the various angulations of the tapers mentioned. Of course the surgeon can then select one block and connect it to the tool 32 and present that block to the spine for determining the space size and shape between adjacent vertebrae, as previously and hereinafter mentioned.

Figure 14:
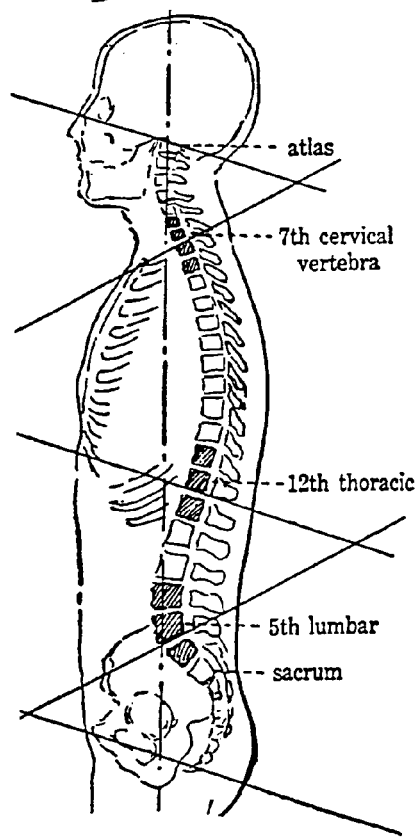
FIG. 14 is a diagrammatic left side view of person and showing the human spinal column with its five extended segments.
Figure 4:
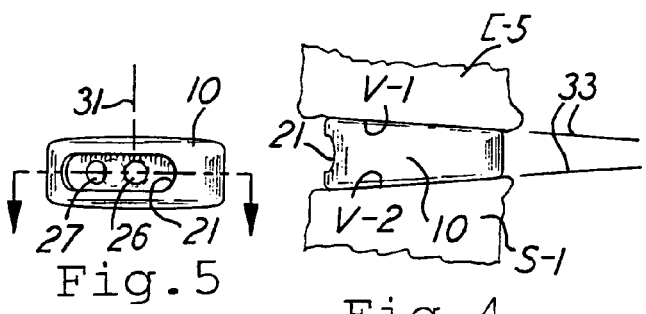
FIG. 4 is a side elevation view of FIG. 3, and showing fragments of two adjacent vertebrae.

FIG. 14 shows a human spine in a person's body, and the usual but different portions along the spinal length are indicated by the shown diagonal lines. Having in mind that the cervical and the lumbar portions are both lordotic, the vertebrae spaced therealong have adjacent surfaces which are angulated relative to each other. That is as shown in FIG. 4 which could be the fifth lumbar L-5 and the first sacrum S-1. Those two adjacent vertebrae have adjacent surfaces V-1 and V-2 which face each other, and, as with all vertebrae in the cervical and lumbar portions, the two adjacent surfaces present an inclusive taper in a greatest height toward the patient's anterior and such as the taper is shown by the lines 33 which are aligned with that shown taper orientation.

It will be understood that the space between the two surfaces V-1 and V-2 has been surgically cleared of the patient's natural spinal disc, and that presents a tapered space between those two adjacent surfaces. The selected block 10 can then be inserted into that vertebrae space to thereby gauge the height and angulation of the space, by sliding between the surfaces V-1 and V-2 as a feeler gauge.

FIG. 4 shows the block disposed between the surfaces V-1 and V-2, and it will be understood that the tool 32 can be attached to the block 10. As shown, the block matches the height and the taper of that space so the surgeon will then select a disc implant (not shown) for permanent insertion into that space upon withdrawal of the trial block 10 from that space. As mentioned with regard to FIG. 4, the hole 26 was used to position the block 10 because the frontal straight approach could be employed to access those two vertebrae. For other vertebrae, hole 27 and its angulated approach, could be used to avoid interference from the patient's body parts in the approach to the spine at other vertebrae along the lordotic structure. In all instances, the smaller height 16 of the block 10 which is being used will be the leading side in the approach into the vertebrae space. With the option of the two holes 26 and 27, the selected block 10 can always be moved into the spinal space by direct anterior to posterior movement when at the spine itself.

Because the blocks 10 are symmetrical and invertible about their respective horizontal planes as viewed in FIGS. 2, 4, and 5, and are therefore reversed when inverted, the approach with the use of the oblique hole 27 can be from either the leftward or rightward side of the patient.

The tool 32 is shown to be elongated and it has a central axis along the section line of FIG. 7. There is a handle 36 shown to be threadedly connected to a two-part sleeve 37 which extends along the tool axis. A shaft 38 is rotatable within the sleeve 37 and there is a shaft threaded end 39 for connecting to a selected one of the blocks 10. Also, there is the inter-locking connection between the sleeve 37 and the relief 24 of each block 10 by virtue of the flat extension 41, as best seen in FIG. 11 which fits into the relief 24. In that arrangement, the block 10 can not rotate about the longitudinal axis and it can therefore be firmly placed relative to the vertebrae, as desired.

The shaft 38 rotates within the sleeve 37 to thereby be threadedly connected to a selected one of the blocks 10, as shown in FIG. 2. Thus the tool 32 at its connection location with the block 10 does not extend beyond the planes of the block surfaces 11 and 12, so the block can be positioned into the vertebrae space without interference from the tool.

A rotator 42 is affixed to the shaft by a set screw 43, and the rotator is rotatable on the sleeve 37 to thereby rotate the shaft 38 and thus threadedly connect the shaft 38 to the block 10 in the selected one of the holes 26 and 27.

The sleeve 37 has distance markings 44 therealong, such as the shown millimeter distances of 20, 30, 40. That shows the surgeon the amount of body penetration of the tool 32.

Each gauge block 10 is preferably circular in its top view, and therefore cylindrical, and each has smooth top and bottom surfaces 11 and 12 which are free of any projections thereon. The holes 22 and 23 have a respective longitudinal axis which is radial to the circular shape, and the holes can be relatively angulated at approximately ten degrees. In the use of either hole 22 and 23, the gauge block will approach the spinal space in the orientation consistent with the lordotic shape of the space, thus the smaller block height will enter the space as a leading edge, in keeping with the lordosis of the patient. The line 17 can be labeled "straight approach" or "frontal approach" or like notation to indicate that alignment with the orientation of the taper.

So there are a plurality of blocks 10 of different heights and tapered shapes, and one tool can be provided to connect with each chosen block. After the correct size of block is inserted to determine the vertebrae space, the block and tool are withdrawn and the permanent implant of the size and shape of the block which fit the space can be installed in place of that gauge block. The lordotic angle, such as shown by the lines 33 and which can be at an angulation of four or six or eight degrees, or the like number.

In the above description, the method of providing the assembly is also disclosed herein. Also, this is the description of the required preferred embodiment, and changes could be made in the described assembly and still be within the scope of the claiming of this invention.

What is claimed is:

1. A spinal gauge block and tool assembly for determining the distance between two adjacent walls on two adjacent vertebrae for the implant of a disc, comprising:
   a spinal gauge block having a tapered configuration formed by a top surface and a bottom surface for respectively contacting the two adjacent walls and with said top surface and said bottom surface respectively extending along two planes which are spaced apart and angled with respect to each other to thereby be non-parallel planes,
   said gauge block having a side surface intermediate said top and bottom surfaces with a first dimension and a second dimension respectively directly between said top and bottom surfaces and with said first dimension being greater than said second dimension and with said dimensions being located in diametrically opposed positions on said gauge block and thereby be located in conformance with the tapered configuration,
   indicia on said gauge block marking the location of said greater dimension, wherein said indicia is a line extending between the locations of said first dimension and said second dimension,
   said side surface having two holes extending therethrough and into said gauge block and with said holes having respective central axes with one of said axes aligned with said indicia and the other of said axes being axially angulated relative to said indicia, and
   a tool having an elongated axis and connectable to said gauge block through a selected one of said holes to thereby provide for two different angulated approaches to the two adjacent vertebrae and relative to said tool elongated axis.

2. The spinal gauge block and tool assembly as claimed in claim 1, wherein:
   said line extending between the locations of said first dimension and said second dimension comprises an arrow head.

3. The spinal gauge block and tool assembly as claimed in claim 1, wherein:
   said holes are threaded holes for alternate screw-reception of said tool.

4. The spinal gauge block and tool assembly as claimed in claim 3, including:
   a non-rotation connection between said gauge block and said tool for restraining rotation of said gauge block about said axis of said tool.

5. The spinal gauge block and tool assembly as claimed in claim 4, wherein:
   said non-rotation is a tongue-and-groove connection for self-engagement upon screwing said tool into either selected one of said holes.

6. The spinal gauge block and tool assembly as claimed in claim 3, including:
   said tool having a sleeve portion and a rotatable threaded portion in said sleeve portion for threaded engagement of said gauge block with said tool, and markings along said tool for determining the depth of penetration of said tool into the patient's body.

7. A spinal gauge block and tool assembly for determining the distance between two adjacent walls on two adjacent vertebrae in preparation for implanting a spine-supporting disc between the two vertebrae, comprising:
   a spinal gauge block having a tapered configuration extending along a plane and having a first side and a second side spaced apart along said plane and with said sides having respective heights and with said height of said first side being greater than said height of second side to thereby present the tapered configuration,
   indicia on said gauge block marking the location of said height of said first side, wherein said indicia is a line extending directly between the locations of said heights of said sides,
   said first side having two holes with respective central axes and extending into said gauge block and with one of said two holes being axially aligned with said indicia and the other of said two holes being axially angulated relative to said indicia, and
   a tool for positioning said gauge block between the two adjacent walls of the two adjacent vertebrae and said tool having an elongated axis and being connectable to said gauge block through a selected one of said two holes to thereby provide for two different angles of approach of said tool elongated axis toward the two adjacent vertebrae and, with the connection of said tool in either one of said two holes, said second side of said gauge block is presented in a leading position of movement toward the vertebrae relative to the remainder of said block and relative to said first side to thereby be pushed to a position between the two adjacent walls on the two adjacent vertebrae before the movement of said first side therebetween.

8. The spinal gauge block and tool assembly as claimed in claim 7, wherein:
   said line extending directly between the locations of said heights of said sides comprises an arrow head.

9. The spinal gauge block and tool assembly as claimed in claim 7, wherein:
   said holes are threaded for alternate screw-reception of said tool and relatively angled approximately ten degrees.

10. The spinal gauge block and tool assembly as claimed in claim 9, including:
   a non-rotation connection between said gauge block and said tool for restraining rotation of said gauge block about said axis of said tool.

11. The spinal gauge block and tool assembly as claimed in claim 10, wherein:
   said non-rotation connection is a tongue-and groove connection for self-engagement upon screwing said tool into either selected one of said two holes.

12. The spinal gauge block and tool assembly as claimed in claim 11, including:
   said tool having a sleeve portion and a rotatable threaded portion in said sleeve portion for threaded engagement of said tool with said gauge block.

13. The spinal gauge block and tool assembly as claimed in claim 12, including:
   a plurality of said gauge blocks of sizes different from each other for determining the distance between the two adjacent walls and being cylindrical in shape, and
   said tool being a single one adapted to individually connect with all of said gauge blocks.

* * * * *

UNITED STATES PATENT AND TRADEMARK OFFICE
CERTIFICATE OF CORRECTION

| | | |
|---|---|---|
| PATENT NO. | : 7,247,169 B1 | Page 1 of 1 |
| APPLICATION NO. | : 10/783430 | |
| DATED | : July 24, 2007 | |
| INVENTOR(S) | : Janzen Lo et al. | |

It is certified that error appears in the above-identified patent and that said Letters Patent is hereby corrected as shown below:

On the Cover Page, item [75], Inventors: "Neffrey C. Wang" should read

--Jeffrey C. Wang--

Signed and Sealed this

Twenty-seventh Day of May, 2008

JON W. DUDAS
*Director of the United States Patent and Trademark Office*